United States Patent
Inoue

(10) Patent No.: US 8,851,674 B2
(45) Date of Patent: Oct. 7, 2014

(54) OPHTHALMOLOGIC APPARATUS, CONTROL METHOD THEREFORE, AND RECORDING MEDIUM STORING METHOD

(75) Inventor: Hiroyuki Inoue, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 178 days.

(21) Appl. No.: 13/598,938

(22) Filed: Aug. 30, 2012

(65) Prior Publication Data

US 2013/0188130 A1 Jul. 25, 2013

(30) Foreign Application Priority Data

Jan. 25, 2012 (JP) ................................. 2012-012844

(51) Int. Cl.
*A61B 3/14* (2006.01)

(52) U.S. Cl.
USPC .......................................... 351/210; 351/209

(58) Field of Classification Search
USPC ................... 351/210, 209, 208, 206, 205, 246
See application file for complete search history.

(56) References Cited

U.S. PATENT DOCUMENTS

| | | | |
|---|---|---|---|
| 5,644,375 A | 7/1997 | Suzuki | |
| 7,478,909 B2 | 1/2009 | Masaki | |
| 7,695,139 B2 | 4/2010 | Ishikura | |
| 2004/0156019 A1 | 8/2004 | Masaki | |
| 2007/0146636 A1 | 6/2007 | Ishikura | |
| 2012/0218520 A1 | 8/2012 | Inoue | |
| 2012/0327365 A1* | 12/2012 | Makihira | ...................... 351/206 |

FOREIGN PATENT DOCUMENTS

| | | |
|---|---|---|
| CN | 1518948 A | 8/2004 |
| CN | 1989894 A | 7/2007 |
| GB | 2 293 659 A | 4/1996 |
| JP | 08-012844 A | 1/1996 |
| JP | 9-094226 A | 4/1997 |
| JP | 2001-309888 A | 11/2001 |
| JP | 3468909 B2 | 11/2003 |
| JP | 3610133 B2 | 1/2005 |
| JP | 3779913 B2 | 5/2006 |
| JP | 2009-072513 A | 4/2009 |

OTHER PUBLICATIONS

Sep. 10, 2013 Great Britain Official Action in Great Britain Patent Appln. No. 1301314.9.
May 16, 2013 Great Britain Official Action in Great Britain Patent Appln. No. 1301314.9.
Aug. 5, 2014 Chinese Official Action in Chinese Patent Appln. No. 201310030997.0.

* cited by examiner

*Primary Examiner* — Hung Dang
(74) *Attorney, Agent, or Firm* — Fitzpatrick, Cella, Harper & Scinto

(57) ABSTRACT

Provided is an ophthalmologic apparatus that can realize alignment with high stability when performing continuous automatic alignment. The ophthalmologic apparatus includes: an acquiring portion which acquires specific information of an eye to be inspected; a moving unit which moves the acquiring portion relatively to the eye to be inspected; a first positioning unit which performs positioning between the acquiring portion and the eye to be inspected by controlling the moving unit to move the acquiring portion relatively to the eye to be inspected within a first moving area; and a restriction unit which restricts a moving area of the acquiring portion by the moving unit to a second moving area smaller than the first moving area by controlling the moving unit, when a position relationship between the acquiring portion and the eye to be inspected satisfies a first condition by the first positioning unit.

17 Claims, 11 Drawing Sheets

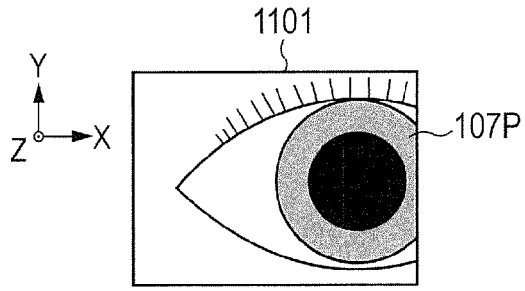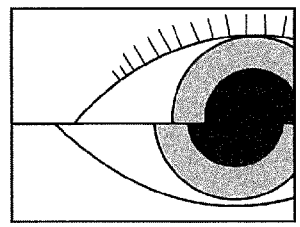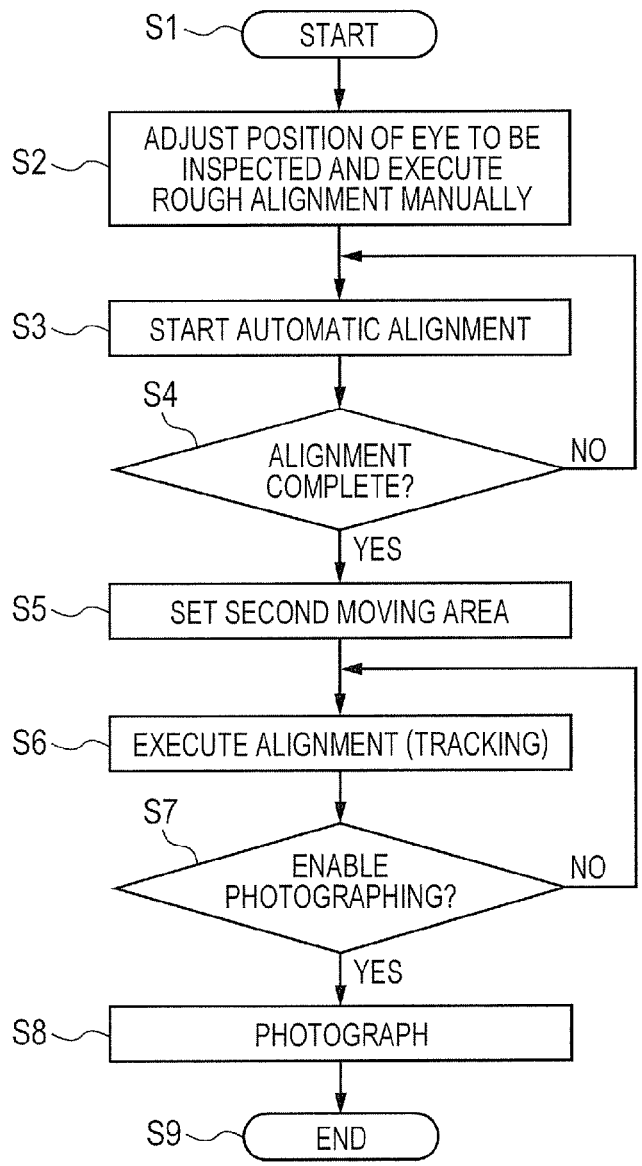

107P  4001  3200

3200

OPHTHALMOLOGIC APPARATUS, CONTROL METHOD THEREFORE, AND RECORDING MEDIUM STORING METHOD

BACKGROUND OF THE INVENTION

1. Field of the Invention

This disclosure relates to an ophthalmologic apparatus, an ophthalmologic control method, and a recording medium.

2. Related Background Art

In an ophthalmologic apparatus for acquiring specific information (measurement, photography, and the like) of an eye to be inspected, it is necessary to align an acquiring portion to the eye to be inspected in a predetermined position relationship. In addition, a human eye moves constantly as a small involuntary movement or a saccadic eye movement even if a line of sight is fixed. Further, visual fixation of a patient eye may be difficult. Therefore, in order to maintain an optimal position relationship between the eye to be inspected and the acquiring portion, it is important to have an alignment action of tracking the eye to be inspected. However, if the eye to be inspected moves largely so as to be shifted in inspection, it is considered that a certain abnormality has occurred. Therefore, in this case, it is not necessary to perform the alignment.

Japanese Patent Application Laid-Open No. 2001-309888 describes an ophthalmologic apparatus that is automatically aligned to the eye to be inspected. In addition, Japanese Patent No. 3,468,909 describes an ophthalmologic apparatus, in which when accidentally entering an alignment start range during adjustment of a mechanism for restricting a movement in a direction of the eye to be inspected, the alignment is not started as natural, but the start of the alignment is disabled as an accident.

If the eye to be inspected moves largely, the ophthalmologic apparatus described in Japanese Patent Application Laid-Open No. 2001-309888 moves the acquiring portion over the entire movable range for performing the alignment. Therefore, despite that the movement of the eye to be inspected is abnormal, the acquiring portion may continue the alignment action to the eye to be inspected so that the alignment action becomes unstable.

On the other hand, in the ophthalmologic apparatus described in Japanese Patent No. 3,468,909, the start of the alignment is disabled when entering the alignment start range. Therefore, it is difficult to continue the alignment control stably on the precondition that the alignment is started when entering the alignment start range.

Further features of the present invention will become apparent from the following description of exemplary embodiments with reference to the attached drawings.

SUMMARY OF THE INVENTION

In view of the above-mentioned problem, it is one of objects of this disclosure to provide an ophthalmologic apparatus that can realize the alignment with high stability when performing continuous automatic alignment. Note that, without limiting to the above-mentioned object, an object to obtain an action and effect derived from each of structures described later for embodying the invention as action and effect that cannot be obtained by the conventional technology is also regarded as one of the objects of this disclosure.

In order to achieve the above-mentioned object, an ophthalmologic apparatus of this disclosure includes: an acquiring portion which acquires specific information of an eye to be inspected; a moving unit which moves the acquiring portion relatively to the eye to be inspected; a first positioning unit which performs positioning between the acquiring portion and the eye to be inspected by controlling the moving unit to move the acquiring portion relatively to the eye to be inspected within a first moving area; and a restriction unit which restricts a moving area of the acquiring portion by the moving unit to a second moving area smaller than the first moving area by controlling the moving unit, when a position relationship between the acquiring portion and the eye to be inspected satisfies a first condition by the first positioning unit.

According to this disclosure, it is possible to provide the ophthalmologic apparatus that can realize the alignment with high stability when performing the continuous automatic alignment. In other words, even if the eye to be inspected has an unstable movement during the alignment, it is possible to suppress the unnecessary alignment action of the acquiring portion, and hence to improve stability of the continuous automatic alignment. In addition, an alignment time period can be shortened so that the through-put can be improved.

BRIEF DESCRIPTION OF DRAWINGS

FIG. 1B is an explanatory diagram of a state where an acquiring portion is shifted in an XY direction with respect to an eye to be inspected, FIG. 1C is an explanatory diagram of a state where the acquiring portion is shifted in a Z direction with respect to the eye to be inspected, and FIG. 1D is an explanatory diagram of an operational flow of the ophthalmologic apparatus according to the embodiment of the present invention.

FIG. 5A is a diagram in a case where it is determined whether or not to expand a second moving area based on an elapsed time of the tracking, FIG. 5B is a diagram in a case where it is determined whether or not to expand the second moving area based on the number of times that a misalignment amount is determined to be a predetermined amount or larger, FIG. 5C is a diagram in a case where the second moving area is displaced in synchronization with the movement of the eye to be inspected, FIG. 5D is an explanatory diagram of recording and analyzing a locus of the movement of the eye to be inspected so as to calculate a gravity center of the movement, and FIG. 5E is an explanatory diagram of making an original point of the second moving area be agreed with the gravity center of the movement of the eye to be inspected.

DESCRIPTION OF THE EMBODIMENTS

Preferred embodiments of the present invention will now be described in detail in accordance with the accompanying drawings.

First Embodiment (Configuration of Main Body)

Figure 2A:
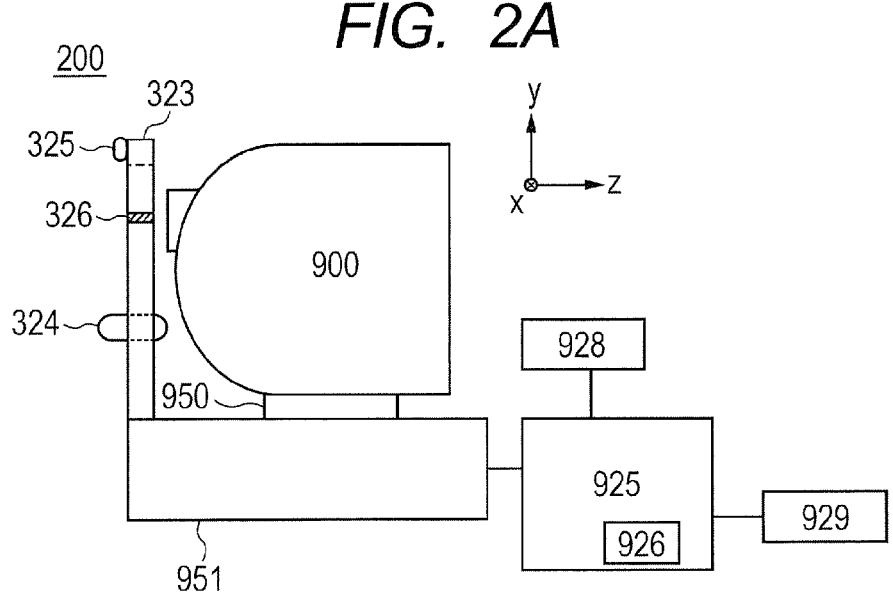
FIG. 2A is an entire schematic diagram of the ophthalmologic apparatus according to this embodiment.

FIG. 2A is a side view of an ophthalmologic apparatus according to a first embodiment. Reference numeral 200 denotes an ophthalmologic apparatus; 900, an acquiring portion (measurement optical system) for acquiring an anterior segment image as well as a two-dimensional image and a tomographic image of a fundus; and 950, a stage portion as a moving portion that can move the acquiring portion 900 in X, Y, and Z directions using motors (not shown). Reference numeral 951 denotes a base portion in which a spectroscope described later is contained.

Reference numeral 925 denotes a personal computer that works both as a control portion for the stage portion and as an alignment unit (a first alignment unit and a second alignment unit described later), and performs control of the stage portion, control of the alignment action, construction of tomographic images described later, and the like. Reference numeral 926 is a hard disk that stores a program for tomographic photography and the like, and also works as a subject information storage portion.

Reference numeral 928 denotes a monitor as a display portion, and reference numeral 929 denotes an input portion by which an instruction to the personal computer is input and which is specifically constituted of a keyboard and a mouse. Reference numeral 323 denotes a face rest including a chin rest 324 that can be moved up and down by a motor (not shown), a forehead rest 325, and an eye height line 326 disposed at the middle in the height direction of a moving area of an objective lens described later. The chin of a subject is placed on the chin rest 324, the forehead of the subject is brought into contact with the forehead rest 325, and the face of the subject is settled so that the height of the eye of the subject becomes substantially the same as the height of the eye height line 326. Thus, the eye to be inspected can be substantially positioned to the acquiring portion 900.

(Configurations of Measurement Optical System and Spectroscope)

Figure 2B:
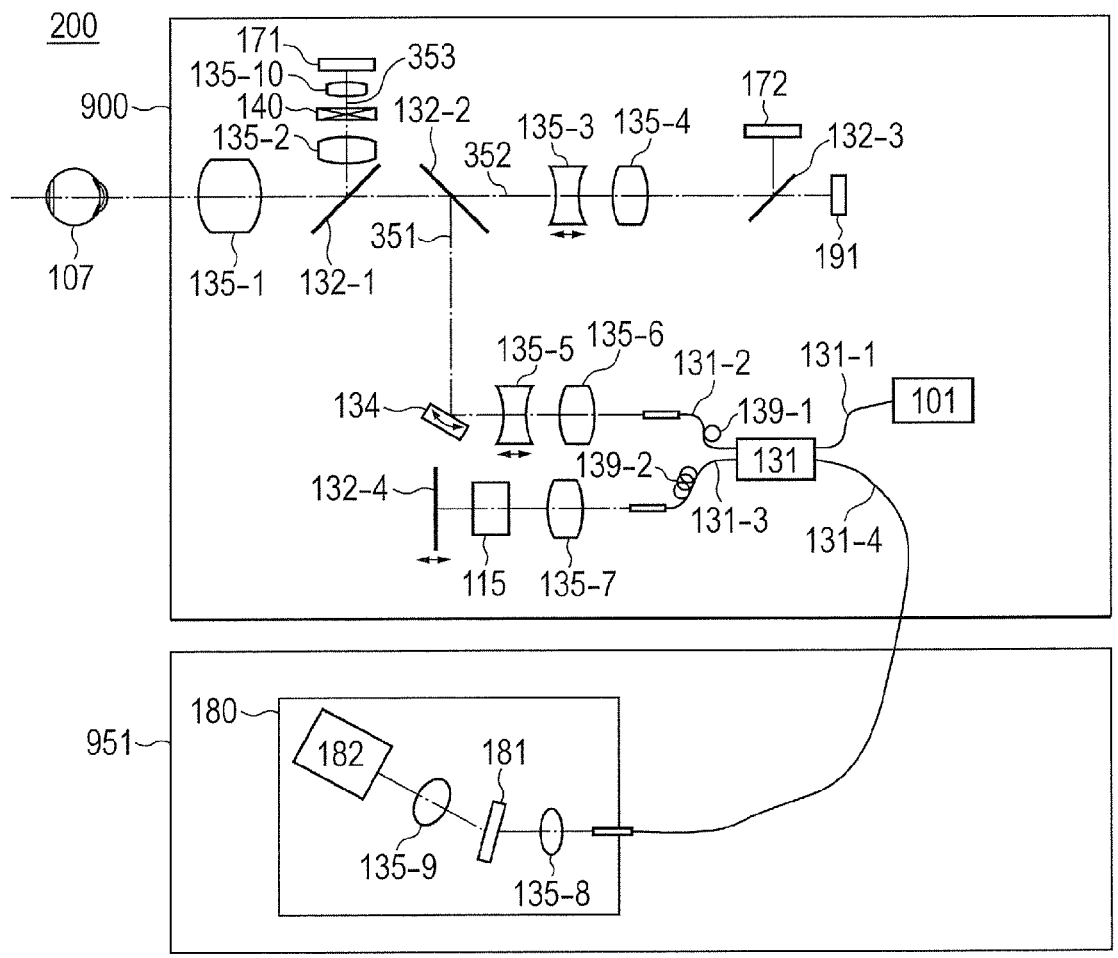
FIG. 2B is an explanatory diagram of a measurement optical system as the acquiring portion of the ophthalmologic apparatus according to this embodiment.

Configurations of the measurement optical system and the spectroscope of this embodiment are described with reference to FIG. 2B. First, an inside of the acquiring portion 900 is described. An objective lens 135-1 is disposed to be opposed to an eye to be inspected 107. On the optical axis of the objective lens 135-1, a first dichroic mirror 132-1 and a second dichroic mirror 132-2 are disposed. Those dichroic mirrors separate the optical path into an optical path 351 of an OCT optical system, an optical path 352 for fundus observation and a fixation lamp, and an optical path 353 for anterior segment observation in accordance with their wavelength bands.

The optical path 352 is further split by a third dichroic mirror 132-3 into an optical path to a CCD 172 for fundus observation and an optical path to a fixation lamp 191 in accordance with their wavelength bands in the same manner as described above. Here, reference numerals 135-3 and 135-4 denote lenses, and the lens 135-3 is driven by a motor (not shown) for focusing of the fixation lamp and fundus observation. The CCD 172 has a sensitivity at a wavelength of fundus observation illumination light (not shown), specifically at a wavelength of approximately 780 nm. On the other hand, the fixation lamp 191 generates visible light so as to prompt the subject to stare.

In the optical path 353, reference numerals 135-2 and 135-10 denote lenses; 140, a split prism; and 171, a CCD for anterior segment observation for detecting infrared light. This CCD 171 has a sensitivity at a wavelength of anterior segment observation illumination light (not shown), specifically at a wavelength of approximately 970 nm. The split prism 140 is disposed at a position conjugate with the pupil of the eye to be inspected 107, and hence a distance of the acquiring portion 900 in a Z direction (front and rear direction) with respect to the eye to be inspected 107 can be detected as a split image of the anterior segment.

The optical path 351 constitutes the OCT optical system as described above, and is used for photographing a tomographic image of the fundus of the eye to be inspected 107. More specifically, the optical path 351 is used for acquiring an interference signal for forming the tomographic image. Reference numeral 134 denotes an XY scanner for scanning the fundus with light. The XY scanner 134 is illustrated as a single mirror but is a galvano-mirror for scanning in two directions of X and Y axes.

Reference numerals 135-5 and 135-6 denote lenses, and the lens 135-5 is driven by a motor (not shown) so as to focus light from an OCT light source 101 emerging from a fiber 131-2 connected to an optical coupler 131 on the fundus 107. By this focusing operation, light from the fundus 107 forms images simultaneously as a spot on an end of the fiber 131-2 and enters the fiber 131-2.

Next, configurations of an optical path from the OCT light source 101, a reference optical system, and the spectroscope are described.

Reference numeral 101 denotes the OCT light source; 132-4, a reference mirror; 115, a dispersion compensating glass; 131, the optical coupler; 131-1 to 131-4, single-mode optical fibers connected and integrated to the optical coupler; 135-7, a lens; and 180, a spectroscope.

These elements constitute a Michelson interferometer. The light emitted from the OCT light source 101 passes through the optical fiber 131-1 and is split by the optical coupler 131 into measuring light on the optical fiber 131-2 side and reference light on the optical fiber 131-3 side.

The measuring light irradiates the fundus of the eye to be inspected 107 as an observation target via the above-mentioned optical path of the OCT optical system and is reflected or scattered by the retina to reach the optical coupler 131 via the same optical path.

The optical coupler 131 combines the measuring light with the reference light to be interference light. Here, the interference occurs when an optical path length of the measuring light becomes almost the same as an optical path length of the reference light. The reference mirror 132-4 is retained in an adjustable manner in an optical axis direction by a motor (not shown) and a drive mechanism (not shown), and hence the optical path length of the reference light can be adjusted to the optical path length of the measuring light that varies depending on the eye to be inspected 107. The interference light is guided to the spectroscope 180 via the optical fiber 131-4.

In addition, reference numeral 139-1 denotes a polarization adjustment portion on the measuring light side disposed in the optical fiber 131-2. Reference numeral 139-2 denotes a polarization adjustment portion on the reference light side disposed in the optical fiber 131-3. The polarization adjustment portions include some parts in which the optical fiber is looped, and the looped part is turned about a longitudinal direction of the fiber so that the fiber is twisted. Thus, polarized states of the measuring light and the reference light can be adjusted respectively to the same state.

The spectroscope 180 is formed of lenses 135-8 and 135-9, a diffraction grating 181, and a line sensor 182. The interference light emerged from the optical fiber 131-4 becomes collimated light via the lens 135-8, and is then diffracted by the diffraction grating 181 so as to form images on the line sensor 182 via the lens 135-9.

Next, a periphery of the OCT light source 101 is described. The OCT light source 101 is a super luminescent diode (SLD) that is a typical low coherent light source. The center wavelength is 855 nm, and the wavelength band width is approximately 100 nm. Here, the band width is an important parameter because it affects a resolution of the acquired tomographic image in the optical axis direction.

The SLD is selected as a type of the light source here, but it is sufficient as long as the light source can emit low coherent light. It is possible to use an amplified spontaneous emission (ASE) or the like. As to the center wavelength, near infrared light is suitable in view of measuring an eye. In addition, because the center wavelength affects the resolution of the acquired tomographic image in a lateral direction, it is desired that the wavelength be as short as possible. The center wavelength is set to 855 nm because of the both reasons.

The Michelson interferometer is used in this embodiment, but a Mach-Zehnder interferometer may be used. In accordance with a light intensity difference between the measuring light and the reference light, it is desired to use the Mach-Zehnder interferometer when the light intensity difference is large, and to use the Michelson interferometer when the light intensity difference is relatively small.

(Method of Photographing Tomographic Image)

A method of photographing the tomographic image using the ophthalmologic apparatus 200 is described. The ophthalmologic apparatus 200 can photograph the tomographic image of a predetermined part of the eye to be inspected 107 by controlling the XY scanner 134. First, measuring light scans in an X direction in the figure so that the line sensor 182 photographs information of a predetermined number of lines in a photographing range of the fundus in the X direction. The fast Fourier transform (FFT) is performed on a luminance distribution on the line sensor 182 obtained at a certain position in the X direction, and information obtained by the FFT from the linear luminance distribution is converted into density or color information to be displayed on the monitor 928. This converted information is referred to as an A-scan image.

In addition, a two-dimensional image on which a plurality of A-scan images is arranged is referred to as a B-scan image. After a plurality of A-scan images is photographed for constructing one B-scan image, the scan value in a Y direction is moved, and the scanning in the X direction is performed again so that a plurality of B-scan images is acquired.

The plurality of B-scan images or a three-dimensional image constructed from the multiple B-scan images is displayed on the monitor 928 so as to be used for diagnosis of the eye to be inspected by the inspector.

(Capture Screen Displayed on Monitor Before Photography)

Figure 1A:
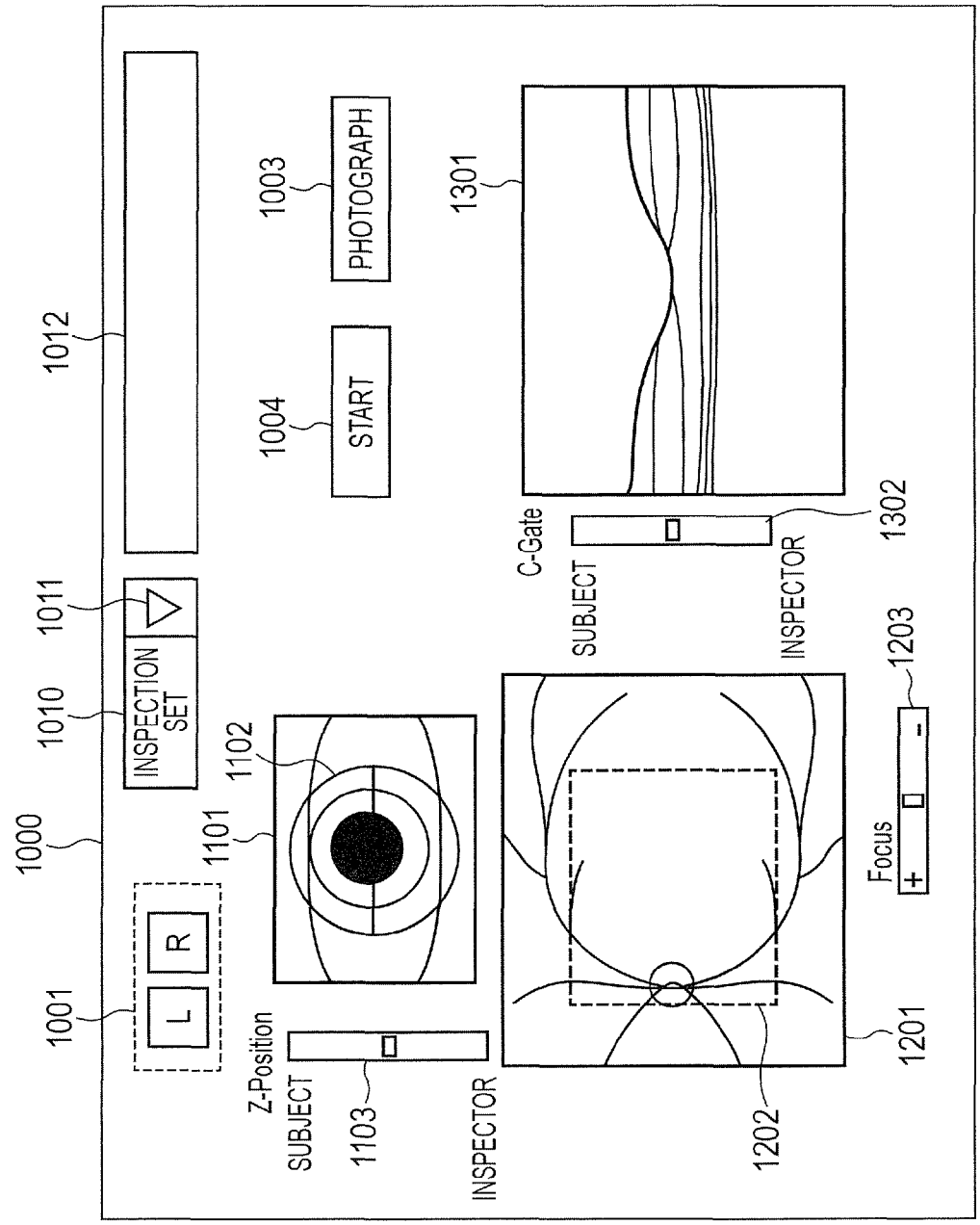
FIG. 1A is an explanatory diagram of a capture screen in an ophthalmologic apparatus according to this embodiment.

With reference to FIG. 1A, the capture screen according to this embodiment is described. The capture screen is a screen for performing various settings and adjustments so as to acquire a desired image of the eye to be inspected, and is a screen displayed on the monitor before photography. Reference numeral 1101 denotes an observation screen for the anterior segment obtained by the anterior segment observation CCD 171; 1201, a display screen for a two-dimensional fundus image obtained by the fundus observation CCD 172; and 1301, a tomographic image display screen for checking the acquired tomographic image. Reference numeral 1001 denotes buttons for switching between both eyes to be inspected. When an L button or an R button is pressed, the acquiring portion 900 is moved to an initial position for the left or right eye.

Reference numeral 1010 denotes an inspection set selection screen, which displays the selected inspection set. In order to change the inspection set, the inspector clicks 1011 so as to display a pull-down menu (not shown) and selects a desired inspection set. In addition, a scan pattern display screen 1012 displays an outline of the scan pattern performed by the currently selected inspection set, for example, a horizontal scan, a vertical scan, a cross scan, and the like.

When an arbitrary point on the anterior segment observation screen 1101 is clicked by the mouse, the acquiring portion 900 is moved so that the point becomes a center of the screen. Thus, alignment between the acquiring portion and the eye to be inspected is performed.

Reference numeral 1004 denotes a start button. When this button is pressed, acquiring of the two-dimensional image and the tomographic image is started. The acquired images of the eye to be inspected are displayed in real time on the two-dimensional image display screen 1201 and the tomographic image display screen 1301. A slider disposed in the vicinity of each of the images is used for adjustment. A slider 1103 is used for adjusting a position of the acquiring portion in the Z direction with respect to the eye to be inspected, a slider 1203 is used for focus adjustment, and a slider 1302 is used for adjusting a coherence gate position.

The focus adjustment is an adjustment of moving the lenses 135-3 and 135-5 in the illustrated arrow directions so as to adjust focus on the fundus. The coherence gate adjustment is an adjustment of moving the reference mirror 132-4 in the illustrated arrow direction so that the tomographic image is observed at a desired position on the tomographic image display screen. By these adjustment operations, the inspector can create a state where an optimal photography can be performed. Reference numeral 1003 denotes a photography button, which is pressed for performing a desired photography after various adjustments are completed.

(Alignment Action)

Hereinafter, there is described a series of actions to align the acquiring portion 900 to the eye to be inspected 107 in three-dimensional directions (an X direction as a left and right direction, a Y direction as an up and down direction, and a Z direction as a front and rear direction) with reference to FIGS. 1B and 1C. Here, concerning a first moving area and a second moving area described later, alignment control in the first moving area is referred to as a first alignment control, and alignment control in the second moving area is referred to as a second alignment control. Using the first alignment control and the second alignment control in order, it is possible to improve stability of continuous automatic alignment.

1-1) First Alignment Control Using First Positioning Unit

The personal computer 925 as a first positioning unit (see FIG. 2A) controls the moving unit 950 to move the acquiring portion 900 within a first moving area 3100 (see FIG. 3B), and positioning between the acquiring portion 900 and the eye to be inspected is performed as follows.

If the acquiring portion is shifted in the XY direction with respect to the eye to be inspected, an anterior segment image (photographed by the anterior segment observation CCD 171) that is displayed in the anterior segment observation screen 1101 of a capture screen 1000 is displayed at a position deviated from the center of the screen as illustrated in FIG. 1B. From here, an alignment detection unit (including the anterior segment observation CCD 171 as a photographing unit and the personal computer 925 as an image processing unit of the photographed anterior segment image) detects a gravity center position of a pupil 107P and calculates a misalignment amount between the eye to be inspected and the acquiring portion 900 in the XY direction.

In addition, if a Z direction distance is shifted, an image is split in the up and down of a field of view as illustrated in FIG. 1C. Therefore, based on the split amount and the split direction, a misalignment amount in the Z direction and a shift direction to front or rear are calculated. Note that, the detection in the Z direction may be performed not only by detecting the split but also, for example, by radiating spot light to the cornea of the eye to be inspected so as to detect a position in the Z direction from a position of the reflection light, or a misalignment may be determined from a degree of blur of the reflection spot light.

By this alignment detection unit, the amount and direction of the misalignment between the acquiring portion 900 and the eye to be inspected can be obtained. Based on a result of the detection by the alignment detection unit, the moving unit 950 moves the stage portion relatively to the eye to be inspected for performing the alignment control.

1-2) First Moving Area

Figure 3A:
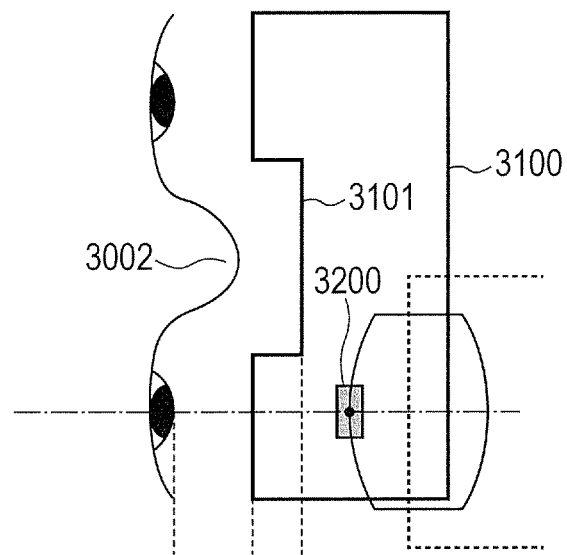
FIG. 3A is a top view of a first moving area according to this embodiment.
Figure 3B:
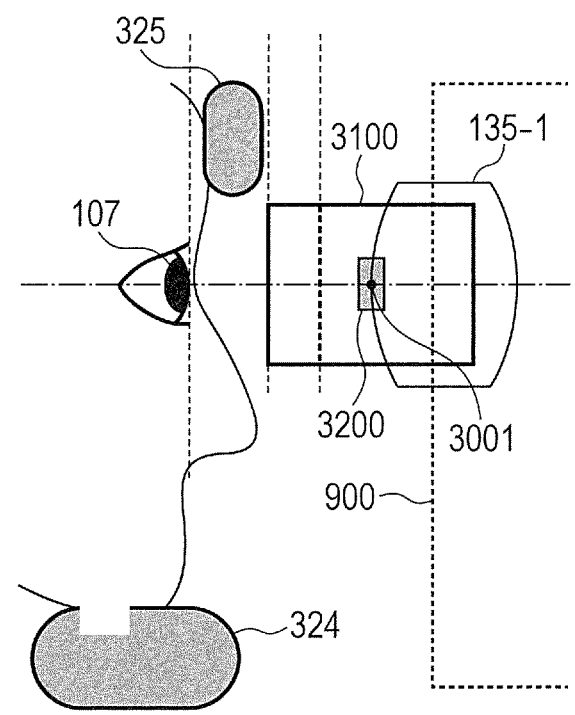
FIG. 3B is a side view thereof.
Figure 3C:
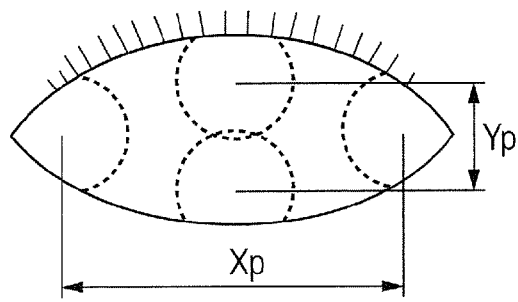
FIG. 3C is an explanatory diagram of the first moving area of the eye to be inspected viewed from front.

Here, the first moving area in which the first alignment control is performed is described with reference to FIGS. 3A to 3C. FIG. 3A is a diagram viewed from above (from the head of the subject), FIG. 3B is a diagram viewed from side, and FIG. 3C is a diagram viewed from front. The stage portion 950 is controlled so that a center point 3001 of the objective lens 135-1 as a reference point of the acquiring portion 900 moves within the first moving area 3100 indicated by the frame line. Note that, the center point 3001 only need be substantially the center of the objective lens 135-1 and may not be identical to the center of the objective lens 135-1.

The subject places his or her chin on the chin rest 324 and set his or her forehead to contact with the forehead rest 325 for undergoing the inspection. Thus, the face of the subject can be stabilized so that a large movement of the eye to be inspected can be suppressed to a certain extent during inspection. In addition, by adjusting a position of the chin rest 324 so as to match with a position of the eye height line 326, the position of the eye to be inspected is roughly adjusted with respect to the acquiring portion, and hence it is possible to reduce time necessary for the alignment.

Here, a feature of the first moving area 3100 is described. The first moving area 3100 is a range where the acquiring portion 900 can move before reaching an alignment completion state in which misalignment of the acquiring portion 900 with respect to the eye to be inspected is within a predetermined permissible range. The first moving area 3100 is set in advance within a largest movable range of the apparatus (in the X, Y, and Z directions). In this embodiment, the first moving area is set to be the same as the largest movable range of the apparatus.

Specifically in this embodiment, the range is set to have a size of 100 mm in the X direction, 30 mm in the Y direction, and 40 mm in the Z direction. The size is set so that the acquiring portion 900 can be aligned with respect to the eye to be inspected 107 of any shape of face. Note that, the first moving area 310 is not limited to the above-mentioned range, but may be smaller than the largest movable range of the apparatus.

The acquiring portion 900 has such a movable range as to be capable of being close to a human eye for measuring the eye, and a nose 3002 of the subject under inspection protrudes toward the acquiring portion as illustrated in the diagram. In this case, the nose of the subject may be unintentionally close to the acquiring portion 900. In order to prevent this, the first moving area 3100 has a recess 3101 in the middle in the X direction so as to be away from the subject in the Z direction.

Here, a method of restricting in the first moving area is described. The stage portion 950 is moved in the X, Y, and Z directions by stepping motors, respectively. The personal computer 925 as the control portion of the stage stores the number of drive pulses of the stepping motor in a memory or the like (not shown) so as to detect a position of the stage portion 950 and to place a restriction.

In addition, it is possible to dispose a sensor (for example, a photointerrupter) in each restriction position, and to detect whether or not the stage portion 950 has passed the sensor position to place the restriction. Further, it is possible to place the restriction mechanically. In this case, a shield for restricting a movement of the stage portion 950 is disposed so that the stage portion cannot physically move beyond the shield, and hence the moving area of the stage portion 950 is restricted.

2) Second Alignment Control Using Second Positioning Unit and Second Moving Area The personal computer 925 as a second positioning unit (see FIG. 2A) controls the moving unit 950 to move the acquiring portion 900 within a second moving area 3200 (see FIGS. 4A to 4F) so as to perform positioning between the acquiring portion 900 and the eye to be inspected as follows.

When it is determined that the first alignment control unit has obtained the alignment completion state in which the misalignment of the acquiring portion 900 with respect to the eye to be inspected becomes within a predetermined permissible range (when a position relationship between the acquiring portion and the eye to be inspected satisfies a first condition), the process proceeds to the second alignment control. In other words, a position of the moving unit 900 in the alignment completion state is set to the origin, and the alignment control is performed based on a result of the detection by the alignment detection unit within the second moving area 3200 (see FIGS. 4A to 4F) smaller than the first moving area.

In a design in which the origin of the second moving area 3200 is shifted from the position of the moving unit 900 in the alignment completion state, a bias occurs in the range that can be tracked when the eye to be inspected displaces from the alignment completion state in any direction of the left, right, up, and down directions. Therefore, it is effective to move the origin of the second moving area 3200 from the position of the moving unit in the alignment completion state for a subject having a feature in movement of the eye to be inspected.

However, in this embodiment, because the origin of the second moving area 3200 is set to the position of the moving unit in the alignment completion state, the apparatus can track the eye to be inspected without a bias even if the eye to be inspected displaces from the alignment completion state in any direction of the left, right, up, and down directions. Note that, it is described that the origin of the second moving area 3200 is set to the position of the moving unit 900 in the alignment completion state, and more specifically, the origin of the second moving area 3200 is the center point 3001 of the objective lens 135-1 in the alignment completion state.

In this way, the second moving area 3200 is set as a range in which the acquiring portion 900 can move for tracking after the alignment to the eye to be inspected is once completed. It is preferred that the second moving area 3200 be set larger than the alignment permissible range and smaller than the first moving area.

The second moving area 3200 is set smaller than the first moving area because the position of the eye to be inspected does not move largely so that only a small movement occurs due to a movement of the line of sight, a small involuntary movement, and the like if the face of the subject is fixed to (in contact with) the chin rest and the forehead rest to a certain extent. Thus, an alignment action after being aligned once, namely unnecessary tracking of the eye to be inspected whose position is largely shifted due to a certain abnormality in the tracking action for tracking the eye to be inspected is omitted, and hence an alignment action can be performed stably. Then, the inspection time period can be shortened so that a load on the subject can be reduced.

Note that, when the eye to be inspected is moved to a position beyond the second moving area 3200, the personal computer 925 may move the acquiring portion 900 to the edge of the second moving area 3200 to follow the movement of the eye to be inspected. In this way, when the eye to be inspected returns to the second moving area 3200 along substantially the same locus, it is possible to restart the tracking promptly. In addition, when the eye to be inspected is moved to a range beyond the second moving area 3200, it is possible to stop the acquiring portion 900 without following the movement of the eye to be inspected. In this way, the acquiring portion 900 is not moved unnecessarily, and hence a more stable alignment action can be performed.

Here, a size of the second moving area 3200 is described with reference to FIG. 4C. FIG. 4C illustrates a position of the pupil when the subject moves the line of sight in the up and down direction or in the left and right direction. A human eye has a movement amount Xp in a horizontal direction larger than a movement amount Yp in a vertical direction. In view of such a movement of the human eye, it is appropriate for tracking to set the second moving area larger in the horizontal direction than in the other direction.

In this embodiment, the second moving area is set to have a size of 20 mm in the X direction, 10 mm in the Y direction, and 10 mm in the Z direction, and the gravity center position of this rectangular block is set to the origin. By setting the second moving area in this way, the movable range can be reduced as much as possible without decreasing trackability to the eye to be inspected, and hence stability of the alignment can be further improved.

Note that, the size of the second moving area 3200 is not limited to the above-mentioned size. For instance, it is considered to set the range of the second moving area in the Y direction to be the same as the range of the first moving area in the Y direction (and, in this case, the range of the second moving area in the X direction and/or in the Z direction is set smaller than the range of the first moving area in the corresponding direction). In this case, even if the inspector changes a position of the chin rest in view of a posture of the subject during the inspection, the tracking can be performed because the moving area in the Y direction is large.

In addition, the range of the second moving area in the X direction may be set to be the same as the range of the first moving area in the X direction, or the moving area of the second moving area in the Z direction may be set to be the same as the range of the first moving area in the Z direction.

The second moving area is not limited to an area having a fixed range but may be one whose range can be expanded or one that can displace to a new origin. In this case, the apparatus (specifically, the personal computer 925) may automatically perform such adjustment, or the inspector may manually perform such adjustment appropriately.

Here, a method of restricting in the second moving area is described. Similarly to the restriction in the first moving area, in the second moving area, the personal computer 925 can also detect a position of the stage portion 950 to place a restriction by storing the number of drive pulses for the stepping motor for driving the stage portion 950. In other words, the personal computer 925 corresponds to an example of a restriction unit that controls the moving unit to restrict a moving area of the acquiring portion by the moving unit to the second moving area smaller than the first moving area.

Note that, when positioning within the second moving area too, similarly to the first positioning unit, for example, a misalignment between the eye to be inspected and the acquiring portion 900 is detected by the personal computer 925, and based on this misalignment, the acquiring portion 900 is moved so that the positioning is performed.

(Pupil Diameter of Eye to be Inspected and Size of Second Moving Area)

In addition, a size of the second moving area 3200 may be changed in accordance with information of the eye to be inspected, for example, a size of the pupil. The size of the pupil can be detected by using the anterior segment observation CCD 171 that also functions as a pupil diameter detection unit in the alignment action. This is described with reference to FIGS. 4A to 4F. Reference numeral 107P denotes the pupil, reference numeral 4001 denotes measuring light passing through the pupil, and reference numeral 3200 denotes the second moving area. In the apparatus for inspecting the fundus of the eye to be inspected, if a diameter of the beam 4001 passing through the pupil is small as illustrated in the diagram, the light can irradiate the fundus even if the position of the pupil is not the center.

Figure 4A:
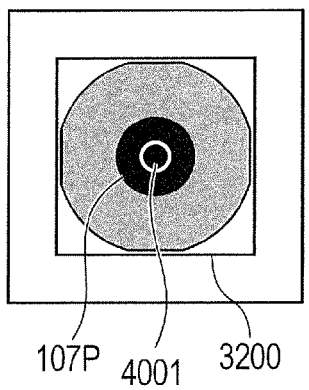
FIGS. 4A to 4C are diagrams of displays on a monitor as a display unit when the pupil is small, respectively illustrating an aligned state, a state where a line of sight of the eye to be inspected is moved, and a state where tracking is performed with respect to the eye to be inspected whose line of sight is moved.
Figure 4B:
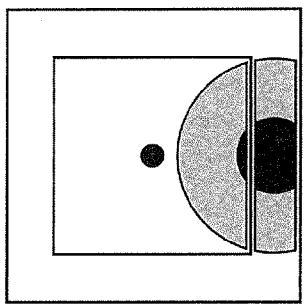
Figure 4C:
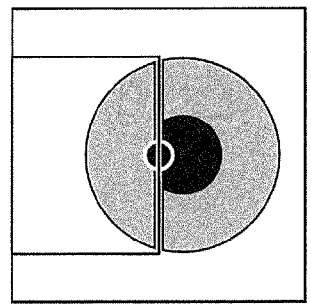

Here, FIGS. 4A, 4B, and 4C illustrate cases where the pupil is small (when the pupil diameter is smaller than a predetermined value). FIG. 4A illustrates a state where the alignment is completed, FIG. 4B illustrates a manner in which the line of sight of the eye to be inspected is moved, and FIG. 4C illustrates a case where the tracking to the moved eye to be inspected is performed. In FIG. 4C, the personal computer 925 that also works as the alignment detection unit detects that a position relationship between the eye to be inspected and the acquiring portion is shifted and calculates the shift amount. Further, the stage portion is driven by the shift amount so that the eye to be inspected and the acquiring portion have an appropriate position relationship (in which the eye to be inspected is positioned in the center).

However, at this time, because there is a restriction by the second moving area 3200, the stage portion cannot be driven until the eye to be inspected is positioned in the center. However, in this case too, because the measuring light 4001 is positioned in the pupil, the measuring light reaches the fundus so that the observation and the inspection can be performed.

Figure 4D:
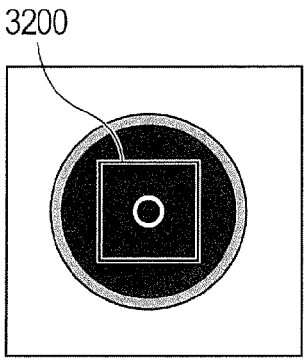
FIGS. 4D to 4F are diagrams when the pupil is large, respectively illustrating an aligned state, a state where the line of sight of the eye to be inspected is moved, and a state where tracking is performed with respect to the eye to be inspected whose line of sight is moved.
Figure 4E:
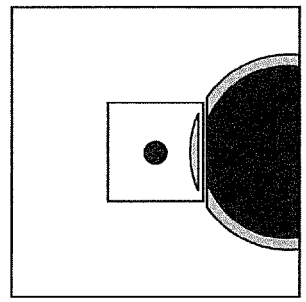
Figure 4F:
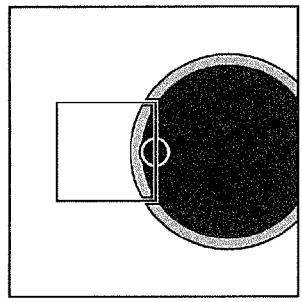

On the other hand, FIGS. 4D, 4E, and 4F illustrate cases where the pupil is large (when the pupil diameter is the predetermined value or larger). FIG. 4D illustrates a case where the eye to be inspected moves by the same amount as FIG. 4E. FIG. 4F illustrates a case where the tracking to the moved eye to be inspected is performed. Here, as illustrated in FIG. 4F, if the pupil is large, the inspection light can enter the pupil even if the misalignment amount between the eye to be inspected and the acquiring portion is large. Therefore, the second moving area 3200 when the pupil is large can be smaller than the second moving area 3200 when the pupil is small as illustrated in FIGS. 4D, 4E, and 4F.

In this way, using the anterior segment observation CCD 171 functioning also as the pupil diameter detection unit in the alignment action, it is possible to detect the size of the pupil and to decrease the size of the second moving area in the XY direction when the pupil is large, based on the detected information. Thus, the range of the tracking action can be reduced within an appropriate range, and hence stability of the alignment action can be further improved so that the inspection time period can be expected to be shortened.

(Line-of-Sight Direction of Eye to be Inspected and Displacement of Second Moving Area)

It is possible to change the original point of the second moving area based on the information of the line-of-sight direction of the eye to be inspected. For instance, it is possible to change the original point of the second moving area based on the presenting position information by a fixation lamp presenting unit. In this embodiment, the acquiring portion includes the fixation lamp 191 for stabilizing the line of sight of the eye to be inspected. The inspector may change a position of the fixation lamp 191 during the inspection so as to perform the observation and the inspection of various parts. In this case, the line of sight of the subject moves along with the position of the fixation lamp 191 so that the pupil position changes.

Therefore, the presenting position of the fixation lamp 191 is obtained, and based on the information, the original point of the second moving area is displaced to be close to the presenting position. Thus, even if the acquired part is changed in the process, the tracking action can be performed stably.

(Both Eyes of Subject and Second Moving Area)

In addition, using the ophthalmologic apparatus, the inspections of both eyes are performed one by one eye in one inspection in most cases. Further, the both eyes are usually symmetric with respect to a vertical center of the face of the subject, namely with respect to a substantial center of the apparatus. Therefore, when the second moving area is determined for one eye and the inspection is performed for the other eye, it is possible to set the second moving area in advance so as to start the alignment based on this information. Thus, the movement in the first alignment is not necessary so that the inspection time period can be shortened.

Note that, when both eyes are measured, the moving area of the measurement unit 900 is switched from the second moving area to the first moving area by pressing the OK button displayed on the display portion 928 for checking a defect in the photograph or by pressing the both eyes switching button 1001.

In this way, the plurality of methods of determining the size of the second moving area is described above. Here, it is considered that a part of the second moving area becomes beyond the first moving area due to factors such as a size of the second moving area, a distance between pupils of the subject, a sunken eye, and the like. In this case, the movement of the stage portion is controlled so that the acquiring portion is not beyond the first moving area, and the stage portion is stopped at a position beyond the first moving area even in the second moving area.

(Operational Flow of Fundus Photography)

An operational flow of the photography in this embodiment is described with reference to FIG. 1D. After starting the inspection in Step S1, the inspector first instructs the subject to place his or her chin on the chin rest 324 and put his or her forehead to contact with the forehead rest 325 in Step S2. Here, the inspector adjusts the height of the chin rest 324 so that a position of the eye of the subject in the height direction is substantially the same as the eye height line 326, and hence adjusts the position of the eye to be inspected to an appropriate position.

Further, the acquired anterior segment image is displayed in real-time on the anterior segment image display screen 1101 of the capture screen 1000, and the inspector can adjust a position of the chin rest 324 and a position of the acquiring portion 900 so that the displayed anterior segment image is substantially within the screen. Here, a drive input to the acquiring portion is performed by clicking the inside of the anterior segment image display screen by a mouse or the like or by using a keyboard or the like as described above. Here, the movable range when the stage portion moves is restricted by the first moving area 3100.

Next, when the inspector clicks the start button 1004 on the capture screen 1000, the process proceeds to Step S3 in which the stage portion 950 starts the automatic alignment action within the first moving area. Here, the alignment detection unit calculates a misalignment amount between the subject and the acquiring portion based on the acquired anterior segment image signal and outputs a drive signal corresponding to the misalignment amount to the drive unit. Thus, the position relationship between the subject and the acquiring portion becomes an appropriate position relationship. Then, the process proceeds to Step S4 for determining whether or not the position relationship between the subject and the acquiring portion has become a predetermined misalignment amount or smaller.

When it is determined in Step S4 that the alignment has not been completed based on the signal from the alignment detection unit, the process returns to Step S3, in which the stage portion 950 is driven again for performing the alignment. On the other hand, when it is determined that the misalignment amount between the eye to be inspected and the acquiring portion has become within a predetermined permissible range so as to be the alignment completion state, the process proceeds to Step S5. There is described here an example in which the alignment action is continued until it is determined that the alignment is completed by the alignment detection unit, but this is not a limitation.

It is possible to set an alignment detection failure time period or the number of the failures in advance, and to warn the inspector to appropriately set a position of the eye to be inspected again if the alignment is not completed within the predetermined time period or number of times. In Step S5, the moving area of the stage portion 950 is changed from the first moving area 3100 to the second moving area 3200. Here, the origin and the size of the second moving area 3200 are as described above, and hence a description thereof is omitted.

Next, in Step S6, the stage portion 950 performs the tracking so that the position relationship between the eye to be inspected and the acquiring portion becomes appropriate in the second moving area 3200. Here, because the second moving area is smaller than the first moving area, it is possible to avoid an unnecessary tracking that may occur when the eye to be inspected moves largely and is positioned outside the moving area. On the other hand, the second moving area is set to a range capable of supporting a movement of the eye to be inspected except an abnormal movement, for example, a movement of the line of sight and the small involuntary movement. Therefore, a stable tracking action can be performed. In addition, various adjustments (not shown), for example, the focus adjustment and the coherence gate adjustment described above, are performed here.

In Step S7, if the position relationship between the eye to be inspected and the acquiring portion becomes a predetermined misalignment amount or smaller in the tracking action, an input by a click or another operation to the photography button 1003 on the capture screen 1000 becomes acceptable, and the photography is started when the inspector performs the input operation. Here, start of the photography is triggered by the inspector's operation, but it is possible that the photography is automatically started when the alignment state and other adjusted states become predetermined states. Here, if the position relationship between the eye to be inspected and the acquiring portion is a predetermined misalignment amount or larger, the process returns to Step S6 in which the tracking is performed again.

After a photography start signal is input, the tomographic image and the fundus image acquired by the fundus observation CCD are stored in the storage device of the personal computer 925 in Step S8, and the process proceeds to Step S9 in which the inspection is completed. By the structure described above, a stable alignment action can be performed continuously. In this embodiment, the OCT apparatus is exemplified for description, but this is not a limitation, and other ophthalmologic apparatus may be used. For instance, the present invention can be embodied also in an ophthalmologic apparatus such as an anterior segment camera, a fundus camera, a refractometer, or a tonometer.

Second Embodiment

Figure 5A:
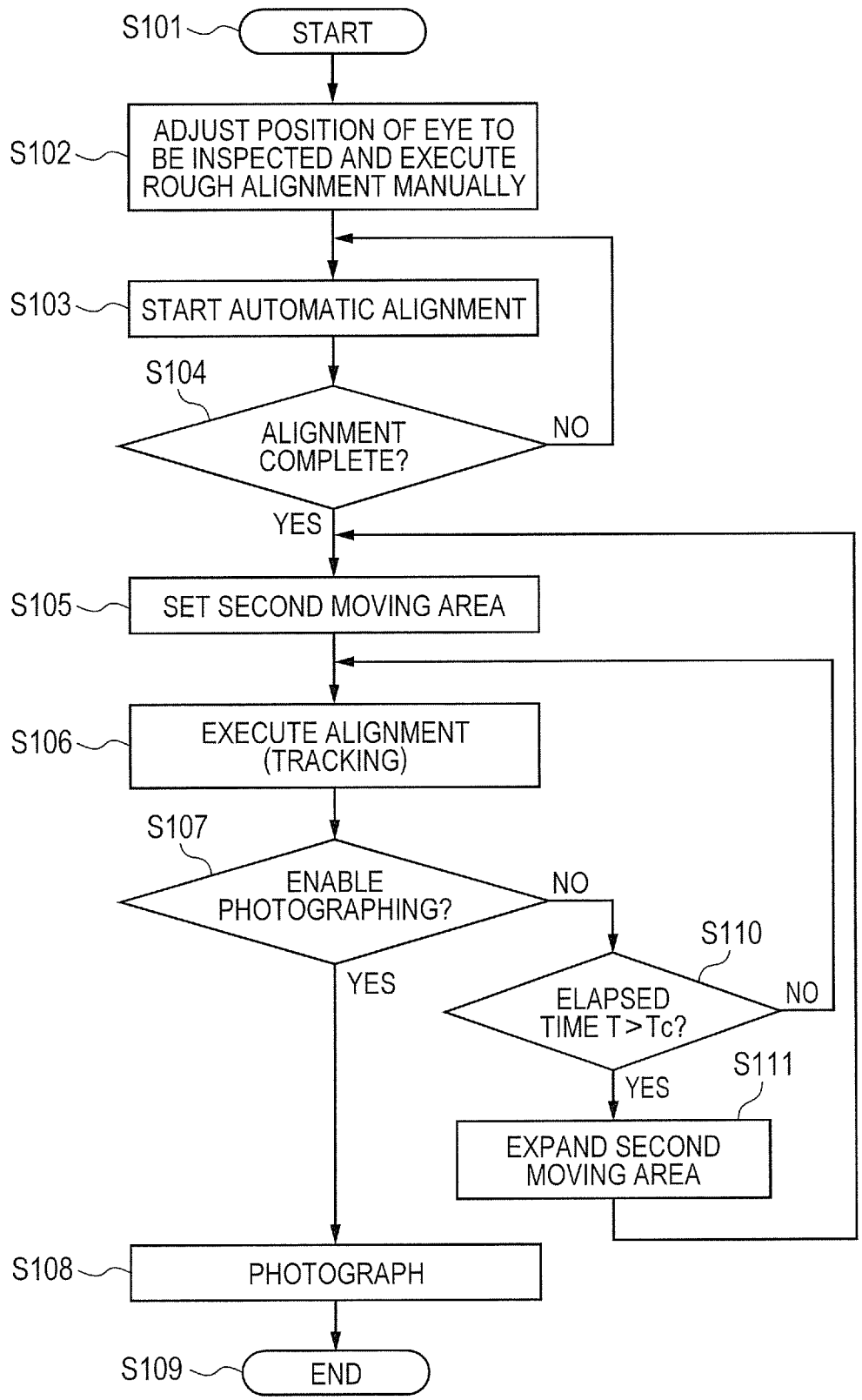
FIGS. 5A to 5E are explanatory diagrams of operational flows according to a second embodiment.

An operational flow of the alignment in a second embodiment is described with reference to FIGS. 5A to 5E. Here, only the operational flow is described. The other structure is the same as that of the first embodiment, and hence a description thereof is omitted. FIG. 5A is an operational flow for supporting the eye to be inspected having a large movement. Steps S101 to S109 are the same as those in the first embodiment, and hence a description thereof is omitted. In this operational flow, when it is determined in Step S107 that the position relationship between the eye to be inspected and the acquiring portion 900 is a predetermined misalignment amount or larger and hence an alignment state enabling the photography is not obtained, the process proceeds to Step S110.

Note that, when it is determined in Step S107 that the position relationship between the eye to be inspected and the acquiring portion 900 is smaller than the predetermined misalignment amount, the process proceeds to Step S108 in which the eye to be inspected is photographed. Note that, the predetermined misalignment amount used for the determination in Step S107 is smaller than the predetermined misalignment amount used for the decision in Step S104, for example.

In Step S110, it is determined whether or not an elapsed time T after starting the tracking time is longer than a predetermined time period Tc. The predetermined time period Tc is stored in the personal computer 925 in advance. It is possible to use a value set before shipment or it is possible that the inspector can set an arbitrary time. When it is determined in Step S110 that the tracking time T is within a predetermined time period (the predetermined time period Tc or shorter), the process returns to Step S106 and the tracking is performed again. On the other hand, if the tracking time T exceeds the predetermined time period Tc, the process proceeds to Step S111.

The state where the alignment state for completing the photography is not achieved in the predetermined time period Tc occurs when a movement of the eye to be inspected is larger than the second moving area 3200. Therefore, in Step S111, the second moving area 3200 is expanded. The new expanded second moving area is larger than the existing second moving area and is smaller than the first moving area.

Here, an expanding amount of the second moving area is determined in advance. It is possible to expand uniformly in the X, Y, and Z directions, or it is possible to expand only in the X and Y directions because a movement of the human eye in the Z direction is small. In addition, because the movement of the human eye is large in the X direction as described above, the expanding amount in the X direction may be set larger than that in other directions so that the second moving area can be expanded more appropriately for the movement of the human eye. After expanding the second moving area in Step S111, the process returns to Step S106, and the tracking is restarted.

Figure 5B:
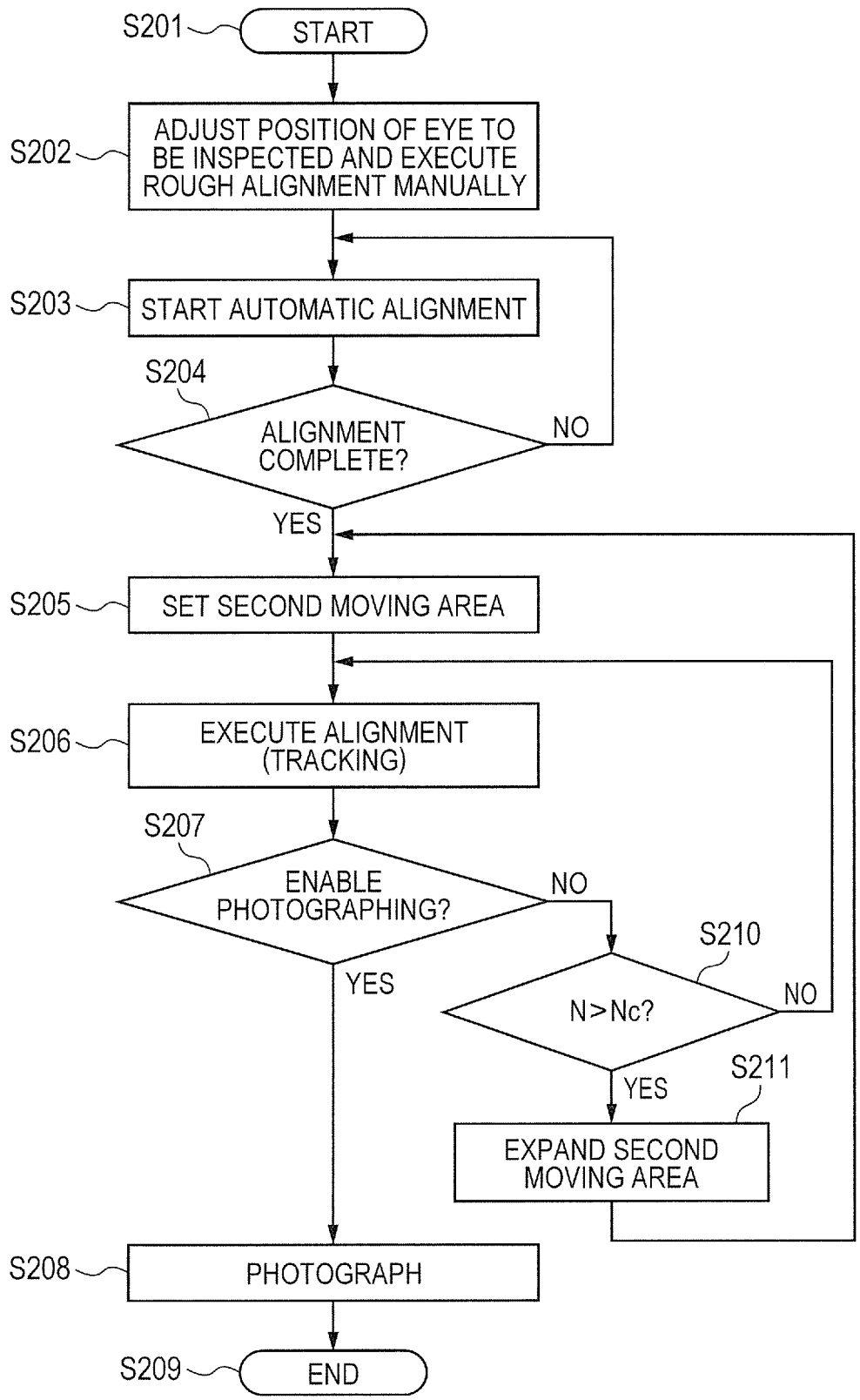

In the above-mentioned embodiment, it is determined whether or not to expand the second moving area based on the elapsed time of the tracking, but this is not a limitation. For instance, it is possible to determine whether or not to expand the second moving area based on the number of times that the alignment detection unit determines that the misalignment amount between the eye to be inspected and the inspecting portion is a predetermined amount or larger as illustrated in FIG. 5B. In other words, the second moving area is expanded in a case where the position relationship between the acquiring portion and the eye to be inspected does not become a state satisfying the second condition by the second positioning unit within a predetermined time period, or a case where the number of times that it is determined that the second condition is not satisfied reaches a predetermined number of times.

This operational flow is described below with reference to FIG. 5B. Steps S201 to S209 in FIG. 5B are the same as those in the operational flow described above, and hence a description thereof is omitted. In this operational flow, the number of times N that it is determined that the misalignment amount between the eye to be inspected and the inspecting portion by the alignment detection unit is a predetermined amount or larger is counted, and it is determined in Step S210 whether or not the number of times N that the alignment detection is NG has exceeded a predetermined number of times Nc. The predetermined number of times Nc is stored in the personal computer 925 in advance. It is possible to use a value set before shipment or it is possible that the inspector can set an arbitrary time.

When it is determined in Step S210 that the number of times N that the alignment is NG is the predetermined number of times Nc or smaller, the process returns to Step S206, and the tracking is performed again. On the other hand, when the number of times N that the alignment is NG has exceeded the predetermined number of times Nc, the process proceeds to Step S211, and the second moving area is expanded. Here, the expanding of the second moving area is already described above, and hence a description thereof is omitted.

By the operational flow as described above, it is possible to enable to track even a large movement of the eye to be inspected. In the embodiment described above, the expanding amount of the second moving area is set in advance, but it is possible to set the expanding amount of the second moving area in accordance with a movement of the eye to be inspected.

Figure 5C:
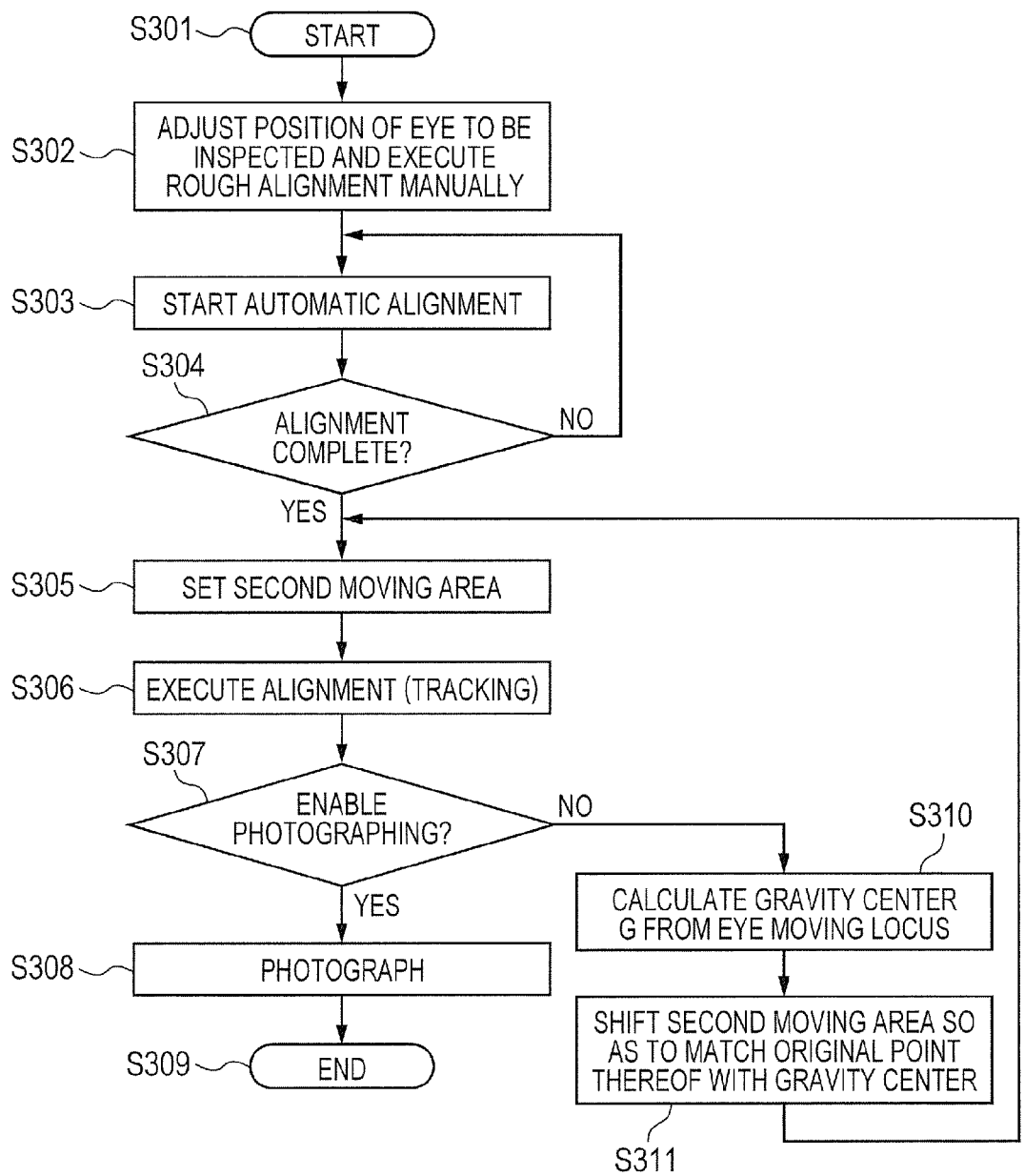

In addition, it is possible to displace the original point of the second moving area without changing a size of the second moving area in accordance with a movement of the eye to be inspected. This displacement of the original point is described below with reference to FIGS. 5C and 5D. Note that, Steps S301 to S309 in FIG. 5C are the same as those in the operational flow described above, and hence a description thereof is omitted.

(Movement of Eye to be Inspected and Displacement of Second Moving Area)

Figure 5D:
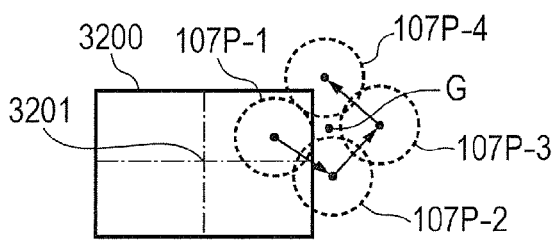

In this embodiment, the anterior segment observation CCD 171 is used as an eye movement detection unit for detecting a movement of the eye to be inspected. In other words, in Step S310 of this operational flow, as illustrated in FIG. 5D, based on information obtained from the anterior segment observation CCD 171, loci of movements 107P-1, 107P-2, 107P-3, and 107P-4 of the eye to be inspected are recorded and analyzed so as to calculate a gravity center G of the movements.

Figure 5E:
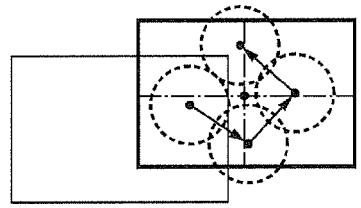

After that, the process proceeds to Step S311. In FIG. 5D, reference numeral 3200 denotes a second moving area, and reference numeral 3201 denotes an original point of the second moving area. In Step S311, as illustrated in FIG. 5E, the original point 53201 of the second moving area is made to be closer to the position in the direction in which the eye to be inspected has moved in Step S310, so as to be the same position as the calculated gravity center G of the movement of the eye to be inspected. After that, the process returns to Step S306, and the tracking is performed again. In this way, the second moving area can be displaced to the position corresponding to the movement of the eye to be inspected, and it is not necessary to expand the second moving area. Therefore, a stable alignment and a tracking action can be realized.

Third Embodiment

An operational flow of the alignment in a third embodiment is described with reference to FIGS. 6A to 6C and 7A to 7C. Here, only the operational flow is described. The other structure is the same as that of the first embodiment, and hence a description thereof is omitted. In addition, in FIG. 6A, Steps S401 to S405 are the same as those in the first and second embodiments, and hence a description thereof is omitted.

Figure 6A:
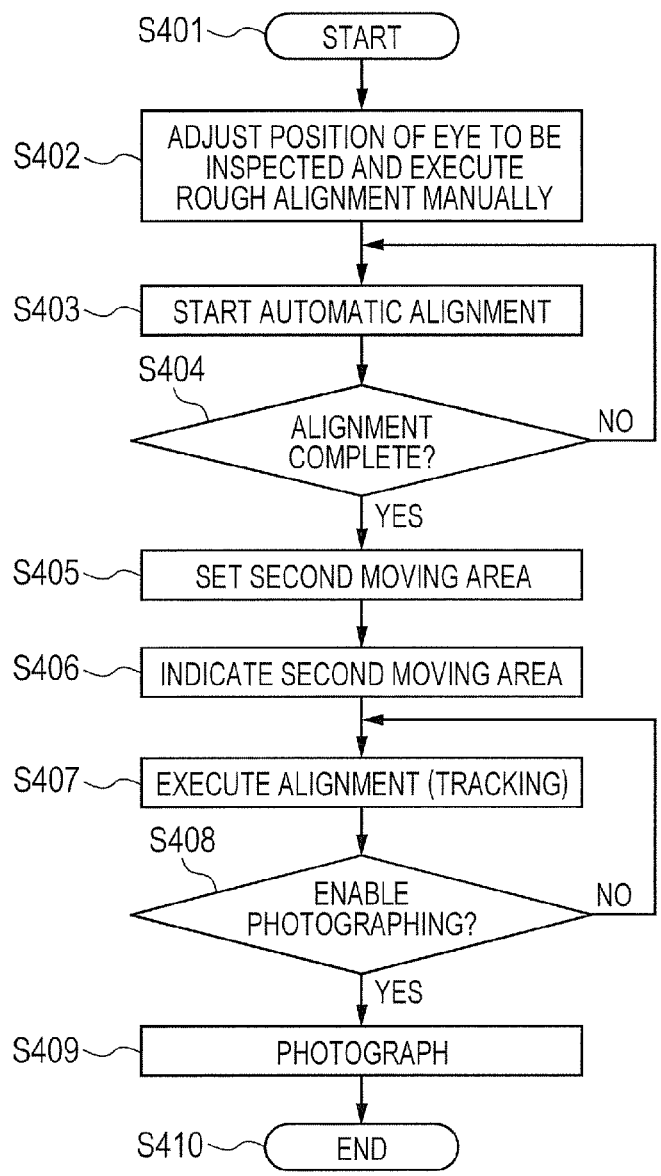
FIG. 6A is an explanatory diagram of an operational flow of displaying a second moving area according to a third embodiment.
Figure 6B:
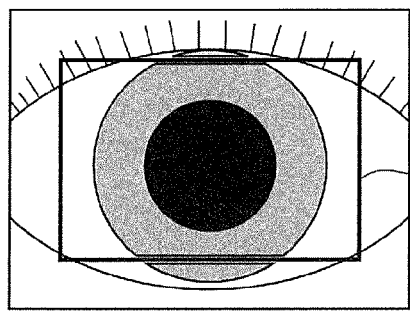
FIG. 6B is an explanatory diagram of displaying the second moving area as a frame line superimposed on an anterior segment image.

In this operational flow, after setting the second moving area in Step S405, as illustrated in FIG. 6B, the second moving area 3200 is displayed and superimposed on the anterior segment image on the anterior segment image display screen 1101 of the capture screen 1000 in Step S406. Note that, the display image illustrated in FIG. 6B is an image that the personal computer 925 illustrated in FIG. 2A functions as a display control unit to control the monitor to display the second moving area 3200 together with the anterior segment image of the eye to be inspected.

Figure 6C:
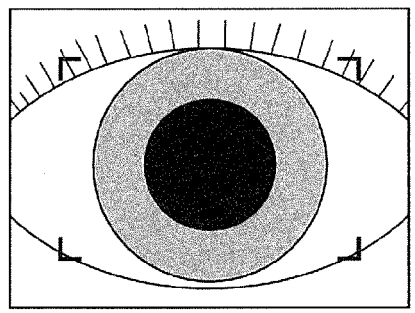
FIG. 6C is an explanatory diagram of displaying the second moving area as four corner marks superimposed on the anterior segment image.

Thus, the inspector can easily determine whether or not the movement of the eye to be inspected is within the second moving area. In addition, with respect to the second moving area, the movement of the subject eye can be relatively compared. Therefore, it is possible to aid to determine whether or not the movement of the eye to be inspected is abnormal. In FIG. 6A, an example of displaying the second moving area by the frame line is illustrated, but it is possible to display marks on four corners as illustrated in FIG. 6C.

Steps S407 to S410 after Step S406 are the same as those in the first and second embodiments, and hence a description thereof is omitted.

In the above description, only the second moving area is displayed. However, if the eye to be inspected is present at a position beyond the second moving area, it is possible to display a warning. An operational flow for displaying a warning is described with reference to FIG. 7A. Steps S501 to S506 are the same as those in the first and second embodiments, and hence a description thereof is omitted.

Figure 7A:
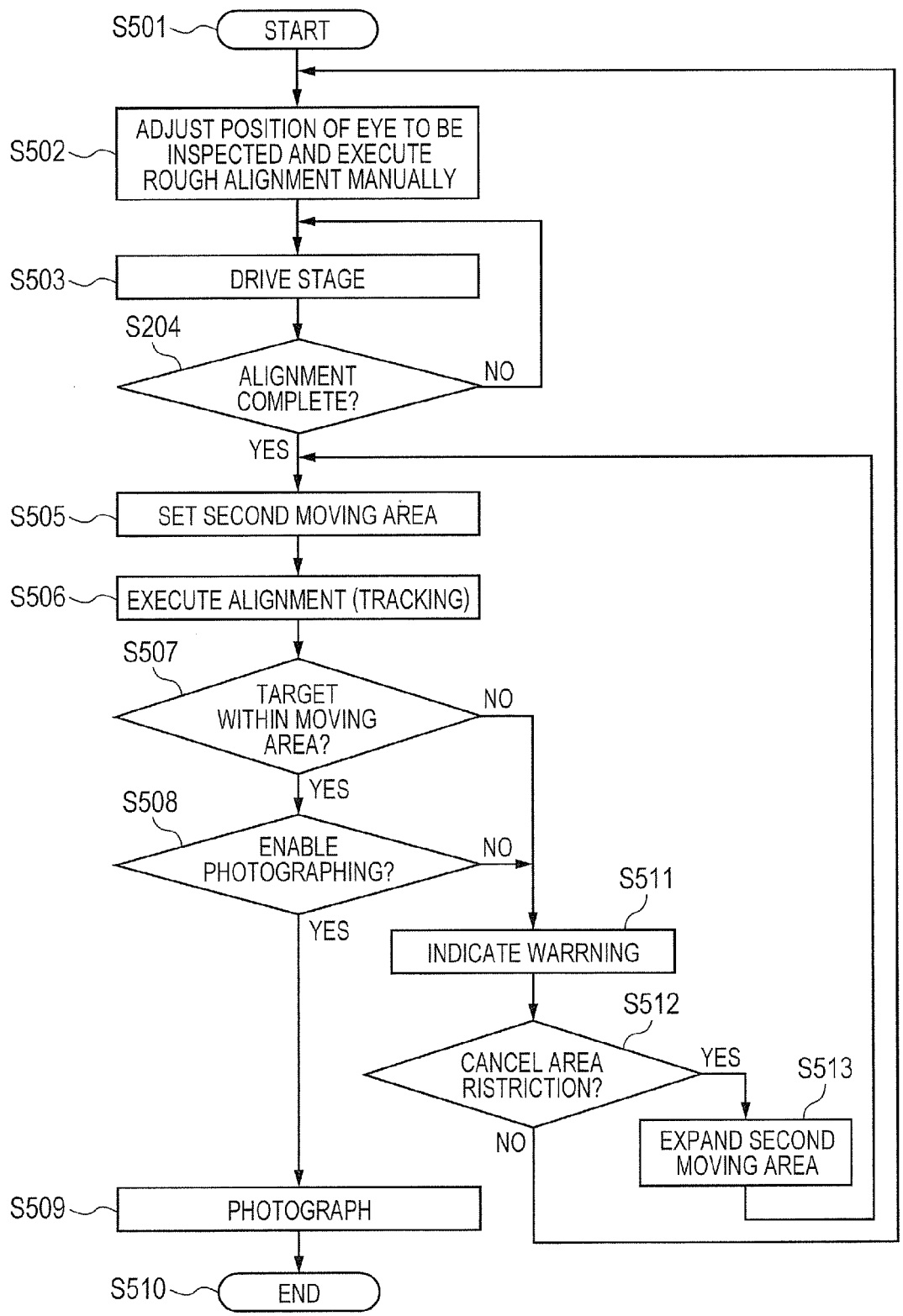
FIG. 7A is an explanatory diagram of an operational flow of displaying a warning when the eye to be inspected exists in a position beyond the second moving area.
Figure 7B:
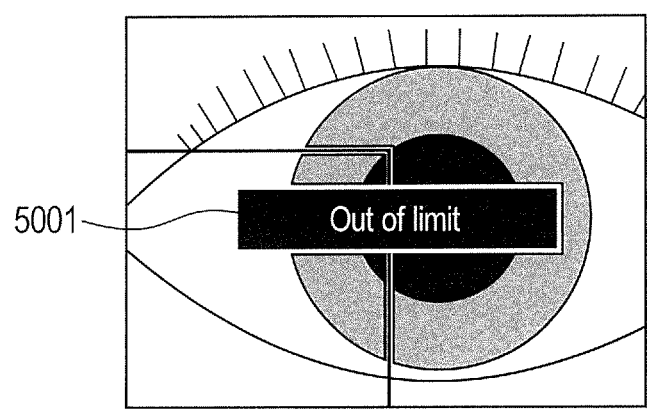
FIG. 7B is an explanatory diagram of a warning display on the monitor when the eye to be inspected exists in the position beyond the second moving area.

When it is detected in Step S507 that a target position of the eye to be inspected is outside the second moving area, or when it is determined in Step S508 that the position relationship between the eye to be inspected and the acquiring portion is a predetermined misalignment amount or larger and hence an alignment state enabling the photography is not obtained, the process proceeds to Step S511. In Step S511, as illustrated in FIG. 7B, a window 5001 for displaying a warning indicating that the eye to be inspected is outside the second moving area is displayed on the capture screen 1000.

Figure 7C:
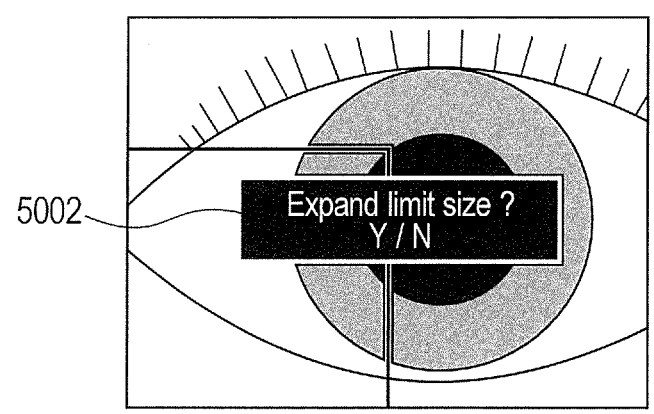
FIG. 7C is a diagram illustrating a selection screen whether or not to expand the second moving area.

Next, the process proceeds to Step S512, and this time, as illustrated in FIG. 7C, a window 5002 for urging the inspector to select whether or not to expand the second moving area is displayed on the capture screen 1000. Here, the inspector determines whether or not to expand the second moving area, and inputs a result of the decision using a mouse or the like. When the selection to expand the second moving area is made, the process proceeds to Step S513 in which expansion of the second moving area is performed as described above in the second embodiment, and the process returns to Step S505. On the other hand, when the selection not to expand the second moving area is made, the process returns to Step S502.

By performing the warning display as described above, the inspector can easily determine whether or not the movement of the eye to be inspected is abnormal. In addition, by performing a display of expanding the moving area together with the warning, it is possible to reflect the intention of the inspector promptly and exactly on the alignment action of the apparatus.

OTHER EXAMPLES

In addition, this example includes, as a further ophthalmologic control method, a step of acquiring specific information of the eye to be inspected, a moving step of moving the acquiring portion relatively to the eye to be inspected, and a step of detecting an alignment state between the acquiring portion and the eye to be inspected. Further, the method includes a first alignment control step of controlling the alignment action within the first moving area based on a result of the detection by the alignment detection unit. In addition, the method includes a step of performing a second alignment control within a smaller second moving area with an original point as a position of the moving unit in the alignment completion state, when it is determined that the alignment completion state is achieved.

In addition, the present invention can be realized also by performing the following process. Specifically, software (program) for realizing the functions of the above-mentioned embodiments is supplied to a system or an apparatus via a network or various storage media, and a computer (or CPU, MPU, or the like) of the system or the apparatus reads and executes the program.

Modified Example 1

Note that, the photography apparatus (OCT) of a fundus tomographic image by optical interference of near infrared laser is described above as the specific information acquiring unit for acquiring specific information of the eye to be inspected in the embodiments, but the present invention is not limited to this. In other words, the present invention can be similarly applied to a fundus camera, a fundus blood flow meter, an eye refracting power measuring apparatus, a cornea shape measuring apparatus, a tonometer, and the like.

Modified Example 2

In the embodiment described above, it is described to display a warning when the eye to be inspected as the target position of the acquiring portion is outside the second moving area, but it is possible to adopt a structure in which an area restriction can be selectively canceled. In this case, it is more preferred that the display unit display to indicate that the state where the area restriction is canceled.

Modified Example 3

In the embodiments described above, the first moving area is the largest movable range of the apparatus, but the present invention is not limited to this. It is possible to adopt a structure in which the first moving area is set to a predetermined range smaller than the largest movable range of the apparatus.

Modified Example 4

In the embodiments described above, the acquiring portion is aligned to the eye to be inspected in the three-dimensional directions (X, Y, and Z directions), but the present invention is not limited to this. It is possible to adopt a structure in which the alignment is performed in the two-dimensional directions (any two directions among the X, Y, and Z directions) or in the one-dimensional direction (any one direction among the X, Y, and Z directions).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-012844, filed Jan. 25, 2012 which is hereby incorporated by reference herein in its entirety.

What is claimed is:

1. An ophthalmologic apparatus, comprising:
an acquiring portion which acquires specific information of an eye to be inspected;
a moving unit which moves the acquiring portion relatively to the eye to be inspected;
a first positioning unit which performs positioning between the acquiring portion and the eye to be inspected by controlling the moving unit to move the acquiring portion relatively to the eye to be inspected within a first moving area; and
a restriction unit which restricts a moving area of the acquiring portion by the moving unit to a second moving area smaller than the first moving area by controlling the moving unit, when a position relationship between the acquiring portion and the eye to be inspected satisfies a first condition by the first positioning unit.

2. An ophthalmologic apparatus according to claim 1, comprising a second positioning unit which performs positioning between the acquiring portion and the eye to be inspected by controlling the moving unit to move the acquiring portion relatively to the eye to be inspected within the second moving area.

3. An ophthalmologic apparatus according to claim 2, wherein when the position relationship between the acquiring portion and the eye to be inspected does not reach a state satisfying a second condition by the second positioning unit within a predetermined time period, or when a number of times that it is determined that the position relationship between the acquiring portion and the eye to be inspected does not satisfy the second condition reaches a predetermined number of times, the second positioning unit expands a range of the second moving area and controls the moving unit to move the acquiring portion in the expanded range so as to perform the positioning between the acquiring portion and the eye to be inspected.

4. An ophthalmologic apparatus according to claim 2, comprising a fixation lamp presenting unit or an eye movement detection unit which detects a movement of the eye to be inspected,
wherein the second positioning unit changes an original point of the second moving area to a presenting position of the fixation lamp presenting unit or a position coming closer to a course in which the eye to be inspected has moved, based on presenting position information of the fixation lamp presenting unit or a signal of the eye movement detection unit, and controls the moving unit to move the acquiring portion in the second moving area having the changed position as a new original point so as to perform the positioning between the acquiring portion and the eye to be inspected.

5. An ophthalmologic apparatus according to claim 1, wherein the second moving area has an original point that is a position of the acquiring portion when the position relationship between the acquiring portion and the eye to be inspected satisfies the first condition by the first positioning unit.

6. An ophthalmologic apparatus according to claim 5, wherein the second moving area can be displaced to a new original point.

7. An ophthalmologic apparatus according to claim 1, comprising a display control unit which controls a display unit to display the second moving area together with an anterior segment image of the eye to be inspected.

8. An ophthalmologic apparatus according to claim 1, wherein the second moving area has a range capable of being expanded.

9. An ophthalmologic apparatus according to claim 1, comprising a pupil diameter detection unit which detects a pupil diameter of the eye to be inspected,
wherein, based on a result of the detection by the pupil diameter detection unit, when the pupil diameter is a predetermined value or larger, the second moving area is set to be a moving area smaller than a moving area of the acquiring portion when the pupil diameter is smaller than the predetermined value.

10. An ophthalmologic apparatus according to claim 1, wherein, when the eye to be inspected is outside the second moving area, a warning is displayed.

11. An ophthalmologic apparatus according to claim 10, wherein the second moving area has a range in a vertical direction that is the same as a range in a vertical direction of the first moving area.

12. An ophthalmologic apparatus according to claim 1, wherein the second moving area has a range larger in a horizontal direction than in other directions.

13. An ophthalmologic apparatus according to claim 1, wherein the first moving area is the same as a largest movable range of the acquiring portion.

14. An ophthalmologic apparatus according to claim 1, wherein, based on information about the second moving area in alignment for one eye, the second moving area for another eye is determined.

15. An ophthalmologic apparatus, comprising:
an acquiring portion which acquires specific information of an eye to be inspected;
a positioning unit which performs positioning between the acquiring portion and the eye to be inspected by moving the acquiring portion relatively to the eye to be inspected; and
a control unit which restricts a movable range of the acquiring portion relative to the eye to be inspected so that the acquiring portion does not move relatively to the eye to be inspected outside the restricted range, when a position relationship between the acquiring portion and the eye to be inspected satisfies a predetermined condition by the positioning unit.

16. An ophthalmologic control method, comprising:
an acquiring step of acquiring specific information of an eye to be inspected by an acquiring portion;
a first positioning step of performing positioning between the acquiring portion and the eye to be inspected by controlling a moving unit for moving the acquiring portion relatively to the eye to be inspected within a first moving area to move the acquiring portion; and
a restricting step of controlling the moving unit to restrict a moving area of the acquiring portion by the moving unit to a second moving area smaller than the first moving area, when a position relationship between the acquiring portion and the eye to be inspected satisfies a first condition in the first positioning step.

17. A non-transitory recording medium having a program recorded thereon, the program causing a computer to execute:
an acquiring step of acquiring specific information of an eye to be inspected by an acquiring portion;
a first positioning step of performing positioning between the acquiring portion and the eye to be inspected by controlling a moving unit for moving the acquiring portion relatively to the eye to be inspected within a first moving area to move the acquiring portion; and
a restricting step of controlling the moving unit to restrict a moving area of the acquiring portion by the moving unit to a second moving area smaller than the first moving area, when a position relationship between the acquiring portion and the eye to be inspected satisfies a first condition in the first positioning step.

* * * * *